(12) United States Patent
Bessiere et al.

(10) Patent No.: US 8,632,821 B2
(45) Date of Patent: Jan. 21, 2014

(54) USE OF XENON FOR TREATING HYPERSENSITIVITY TO PAIN

(75) Inventors: Baptiste Bessiere, Issy les Moulineaux (FR); Guy Simonnet, Bordeaux (FR)

(73) Assignees: L'Air Liquide, Société Anonyme pour l'Etude et l'Exploitation des Procédés Georges Claude, Paris (FR); Université Bordeaux Segalen, Bordeaux (FR)

( * ) Notice: Subject to any disclaimer, the term of this patent is extended or adjusted under 35 U.S.C. 154(b) by 0 days.

(21) Appl. No.: 13/387,285

(22) PCT Filed: Jul. 13, 2010

(86) PCT No.: PCT/EP2010/060021
§ 371 (c)(1),
(2), (4) Date: Jan. 26, 2012

(87) PCT Pub. No.: WO2011/015428
PCT Pub. Date: Feb. 10, 2011

(65) Prior Publication Data
US 2012/0128789 A1    May 24, 2012

(30) Foreign Application Priority Data
Aug. 4, 2009 (FR) ...................................... 09 55476

(51) Int. Cl.
*A61K 33/00* (2006.01)
*A61P 25/00* (2006.01)
(52) U.S. Cl.
USPC ........................................................ 424/613
(58) Field of Classification Search
None
See application file for complete search history.

(56) References Cited

FOREIGN PATENT DOCUMENTS

| FR | 2914633 | * | 10/2008 | ............... A61K 9/72 |
| WO | 0222141 | | 3/2002 | |
| WO | WO 02/22141 | * | 3/2002 | ............. A61K 33/00 |

OTHER PUBLICATIONS

PCT/EP2010/060021, International Search Report dated Oct. 20, 2010.
Angst et al., "Opioid-induced Hyperalgesia", Anesthesiology, vol. 104, No. 3, pp. 570-587 (Mar. 2006).
Chizh et al., "NMDA Antagonists and Neuropathic Pain—Multiple Drug Targets and Multiple Uses", Current Pharmaceutical Design, vol. 11, No. 23, pp. 2977-2994 (2005).
Franks et al "How Does Xenon Produce Anaesthesia?", Nature, vol. 396, p. 324 (Nov. 26, 1998).
Macrae, W.A., "Chronic Pain After Surgery", British Journal of Anaesthesia, 87, pp. 88-98 (2001).
Perkins et al., "Chronic Pain As an Outcome of Surgery", Anesthesiology, vol. 93, No. 4, pp. 1123-1133 (Oct. 2000).
Scholz et al., "Can We Conquer Pain?", Nature Neuroscience, vol. 5, pp. 1062-1067 (Nov. 2002).
Simonnet et al., "Opioid-induced Hyperalgesia: Abnormal or Normal Pain?", NeuroReport, vol. 14, No. 1, pp. 1-7, 20 (Jan. 2003).
Wilder-Smith et al., "Postoperative Hyperalgesia", Anesthesiology, vol. 104, No. 3, pp. 601-607 (Mar. 2006).
Woolf et al., "Neuronal Plasticity: Increasing the Gain in Pain", Science 288, vol. 288, pp. 1765-1769 (Jun. 9, 2000).
French Search Report, FR0955476 issued Apr. 7, 2010.
Ma Daqing et al., "Xenon Exerts Age-Independent Antinociception in Fischer Rats" Anesthesiology: May 2004—vol. 100—Issue 5—pp. 1313-1318 Laboratory Report.
Peterson-Felix S. et al., "Comparison of the Analgesic Potency of Xenon and Nitrous Oxide in Humans Evaluated by Experimental Pain," British Journal of Anaesthesia, vol. 81, No. 5, Nov. 1998, pp. 742-747.
Lee, M.D. et al., "A comprehensive review of opioid-induced hyperalgesia," Pain Physician 14 (2011), pp. 145-161.

* cited by examiner

*Primary Examiner* — Robert A Wax
*Assistant Examiner* — Danah Al-Awadi
(74) *Attorney, Agent, or Firm* — Allen E. White

(57) ABSTRACT

The invention relates to a gaseous mixture containing oxygen ($O_2$) and a volume proportion of 20 to 70% of xenon (Xe) for use as an inhalable drug for preventing or treating hypersensitivity to pain in humans or animals, in particular hypersensitivity to pain expressed as hyperalgesia or allodynia.

7 Claims, 2 Drawing Sheets

*Inflamed paw*

*Non-inflamed paw*

*Inflamed paw*

*Non-inflamed paw*

USE OF XENON FOR TREATING HYPERSENSITIVITY TO PAIN

CROSS-REFERENCE TO RELATED APPLICATIONS

This application is a §371 of International PCT Application PCT/EP2010/060021, filed Jul. 13, 2010, which claims §119 (a) foreign priority to French application 0955476, filed Aug. 4, 2009.

BACKGROUND

The present invention relates to the use of xenon for treating or preventing hypersensitivity to pain and, consequently, pain chronisication.

It is known that, following an inflammation or tissue or nerve damage, a process of pain sensitization will develop and result in hypersensitivity to pain. This is reflected by the appearance of hyperalgesia, i.e. an exaggerated response to a nociceptive stimulation, and/or of allodynia, i.e. a painful sensation brought about by a non-nociceptive stimulus, and persistent pain, as recalled by the articles by C. Woolf et al, *Neuronal plasticity: increasing the gain in pain*, Science, 288, 1765-9 (2000); J. Scholz et al, *Can we conquer pain ?*, Nat Neurosci. 5 Suppl, 1062-7 (2002); and O. Wilder-Smith et al, *Postoperative hyperalgesia: its clinical importance and relevance*, Anesthes., 104, 601-7 (2006).

In the central nervous system (CNS), several experimental and clinical studies have shown an essential role for excitatory amino acids in sensitization to post-traumatic pain via N-methyl-D-aspartate (NMDA) receptors, as recalled by the review B. Chizh et al., *NMDA antagonists and neuropathic pain-Multiple drug targets and multiple uses*, Current Pharmaceutical Design, 11, 2977-94 (2005).

The phenomenon of pain sensitization subsequent to an inflammation or tissue or nerve damage, expressed as hyperalgesia or allodynia and increased pain, is now considered to be the key mechanism responsible for the development of post-operative and chronic pain, as recalled by F. Perkins et al, *Chronic pain as an outcome of surgery. A review of predictive factors*. Anesthesiology 93, 1123-33 (2000); or by W. Macrae, *Chronic pain after surgery*. British Journal of Anaesthesiology, 87, 88-98 (2001).

In particular, during general anesthetics, it is customary to administer volatile or intravenous hypnotics to patients, or intravenous analgesic or opioid substances. Mention may in particular be made of the following anesthetic products which are commonly used in anesthesia, such as fentanyl, alfentanyl, sufentanyl, remifentamil or other opioids, etc.

However, it has been noted that these volatile or intravenous opioids induce and/or amplify post-operative hyperalgesia, which is reflected by sensitivity to pain in patients which is of increased intensity after the operation. It has, moreover, been shown that this opioid-induced greater sensitivity to pain is linked to hyperactivity of the NMDA receptor, as recalled by the articles by Simonnet et al., *Opioid-induced Hyperalgesia: abnormal or normal pain ?* Neuroreport, 14, 1-7, (2003); et Angst et al., *Opioid-induced Hyperalgesia*, Anesthesiology, 104:570-87. (2006).

This effect is notable for a long period, which can in particular be up to 1 year, and therefore results in a decrease in the quality of life of the patients since they will be more sensitive to pain during this time.

In order to attempt to remedy this, document FR-A-2914633 has proposed the use of a gas mixture containing oxygen ($O_2$) and from 2 to 10% by volume of xenon (Xe) for preventing or minimizing post-operative hyperalgesia in humans.

Indeed, xenon, which is an NMDA receptor antagonist, as taught by N. Franks et al, *How does xenon produce anaesthesia ?* Nature, 396, 324. (1998), has an acute analgesic effect, as recalled by D. Ma et al., *Xenon exerts age-independent antinociception in Fischer rats*, Anesthesiology. 100, 1313-8. (2004), and S. Petersen-Felix et al, *Comparison of the analgesic potency of xenon and nitrous oxide in humans evaluated by experimental pain*; Br J Anaesth. 81, 742-7 (1998).

From there, given that NMDA receptors have a major essential role in pain sensitization induced by trauma and amplified by opioids, this property can be used to prevent or treat hypersensitivity to pain, by virtue of the NMDA receptor antagonist properties of xenon used as a pharmacological agent.

However, the solution proposed by FR-A-2914633 is not ideal since the xenon concentrations are too low and do not therefore make it possible to obtain a really effective treatment for preventing or treating hypersensitivity to pain.

Moreover, document WO-A-02/22141 teaches the use of xenon as a cardiovascular protective agent, sedative, analgesic, etc.

In addition, D. Ma et al, *Xenon exerts age-independent antinociception in Fisher rats*, May 2004, Anesth., vol. 100, no 5, pages 1313-1318, show that the analgesic action of xenon is independent of the age of the patients, including in the fetus or the newborn, whereas S. Pertersen-Felix et al, *Comparison of the analgesic potency of xenon and nitrous oxide in humans evaluated by experimental pain*, November 1998, Brit. J. of Anesth., vol. 81, no 5, p. 742-747, compare the analgesic effects of xenon with those of $N_2O$.

SUMMARY

The invention includes both methods and compositions to achieve the desired results, as described, but is not limited to the various embodiments disclosed.

One objective of the invention is to improve the efficacy of treatment for or to prevent hypersensitivity to pain in human beings, namely in particular men, women, children, newborns and the elderly, i.e. to make it possible to prevent, curb or decrease the appearance of this harmful phenomenon of post-operative hyperalgesia or allodynia in patients.

One solution according to the invention is a gas mixture containing oxygen ($O_2$) and a proportion between 20 and 70% by volume of xenon (Xe) for use as an inhaled medicament for preventing or treating hypersensitivity to pain in humans or animals, in particular hypersensitivity to pain reflected by the occurrence of hyperalgesia or allodynia.

Depending on the case, the gas mixture of the invention may comprise one or more of the following characteristics:
- the proportion of xenon is between 22 and 60% by volume;
- the proportion of xenon is between 25 and 60% by volume;
- it consists only of oxygen and xenon or air and xenon;
- it also contains nitrogen, helium, NO, $N_2O$, krypton, argon or neon;
- it contains a proportion by volume of oxygen of between 15 and 25%;
- the hypersensitivity to pain is of post-operative or post-traumatic type;
- the hypersensitivity to pain is induced by at least one opioid;
- it is packaged at a pressure greater than 2 bar in a pressurized container, in particular a gas bottle;

the gas mixture is packaged at a pressure greater than 100 bar in a gas bottle.

The invention also relates to the use of a gas mixture according to the invention containing oxygen ($O_2$) and xenon (Xe) in a proportion of between 20 and 70% by volume, for producing an inhalable medicament for preventing or decreasing hyperalgesia in humans or animals.

The invention also relates, moreover, to a method for treating or preventing hyperalgesia in a patient, comprising the step of administering to said patient, by inhalation, a gas mixture of oxygen and xenon according to the invention.

By virtue of the gas mixture of the invention, it is possible to effectively combat the harmful effect(s) of post-operative or post-traumatic hyperalgesia.

BRIEF DESCRIPTION OF THE DRAWINGS

The invention will now be understood more clearly by means of the examples below and of the description given hereinafter in relation to the attached Figures among which:

FIG. 1A illustrates (for 25% Xe) the threshold of pain perception by rats when a pressure is exerted on the inflamed paw, whereas

FIG. 2A illustrates (for 50% Xe) the threshold of pain perception by rats when a pressure is exerted on the inflamed paw, whereas

EXAMPLES

In order to show the efficacy of the gas mixture according to the invention in the prevention of post-traumatic hyperalgesia, a model of inflammatory pain was used in rats, namely male Sprague-Dawley rats, in the context of preclinical studies.

An inflammatory product, carrageenan (0.2 ml of saline solution with 1% of carrageenan), was injected subcutaneously into the sole of the hind paw of a rat.

Two xenon concentrations by volume were tested, namely:
a ternary gas mixture made up of 25% Xe+25% $N_2$+50% $O_2$, and
a binary gas mixture made up of 50% Xe+50% $O_2$.

The nociceptive threshold, i.e. the pain threshold, was evaluated using the paw-pressure vocalization test (Randall-Selitto), in which increasing pressures (measured in grams) are applied to the hind paw of the rat until the rat squeaks.

More specifically, on Day 0 (D0), the inflammatory product, i.e. the carrageenan (Car), was injected into a hind paw of the rats.

The exposure of the rats to the gases by inhalation begins 1 h 45 after the injection of Car and lasts for 1 h 45. The nociceptive threshold is evaluated 1 h 30, 2 h 30, 3 h 00, 3 h 30 and 4 h 30 after the injection of Car and then once a day until a return to the basal nociceptive threshold.

Figure 1A:
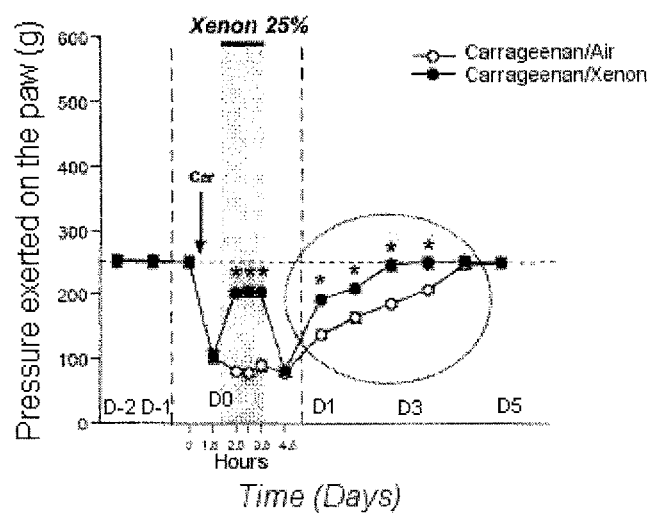
Figure 1B:
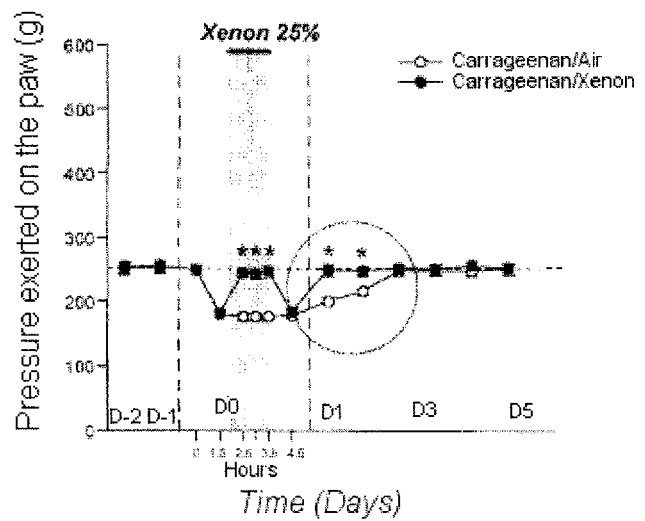
FIG. 1B illustrates (for 25% Xe) this threshold for a non-inflamed paw.

The rats are divided up into groups as follows:

|  | Control | Invention |
|---|---|---|
| Trial 1 (FIG. 1) | Carrageenan/Air | Carrageenan/25% Xenon |
| Trial 2 (FIG. 2) |  | Carrageenan/50% Xenon |

After injection of the inflammatory product (Car), the rats developed hyperalgesia which lasted for 4 days for the inflamed paw and 2 days for the non-inflamed paw. This delayed hyperalgesia results mainly from a pain sensitization process which is NMDA-dependent.

Figure 2A:
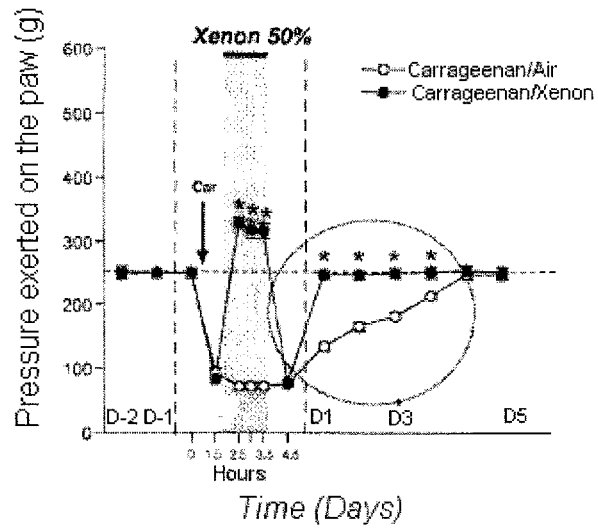
Figure 2B:
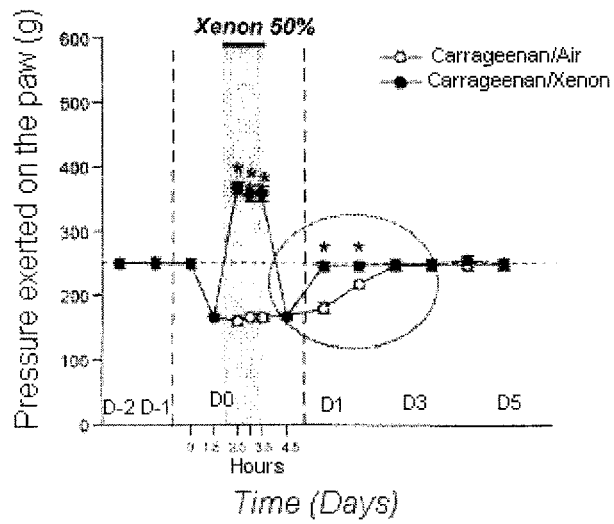
FIG. 2B illustrates (for 50% Xe) this threshold for a non-inflamed paw.

The results obtained (see Figures) show that:
xenon has an analgesic effect during its administration and that a content of 50% (FIG. 2A) is more effective than a content of 25% (FIG. 1A);
xenon has an anti-hyperalgesic effect (circle on Figures) since:
xenon at 25% greatly reduces the delayed hyperalgesia on the inflamed paw (FIG. 1A): 2 days compared with 4 days for the control (air/Car);
xenon at 50% totally prevents the delayed hyperalgesia on the inflamed and non-inflamed paws (FIGS. 2A and 2B).

This demonstrates that xenon prevents the pain sensitization process by virtue of its anti-hyperalgesic properties with respect to the delayed hyperalgesia in the inflamed paw.

Furthermore, xenon also completely prevents the delayed hyperalgesia on the non-inflamed paws, which indicates a central effect of xenon on pain sensitization.

Xenon can therefore be used as a medicament for preventing post-traumatic hyperalgesia and chronic pain.

The gas mixture of the invention containing oxygen $O_2$ and a proportion by volume of 20 to 70% of xenon can therefore be used in the context of a method for prevention or therapeutic treatment, in which the gas mixture is administered by inhalation so as to prevent or treat hypersensitivity to pain in humans or animals, in particular men, women or children, in particular post-operative or post-traumatic hyperalgesia.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method of treating hypersensitivity to pain in humans or animals comprising the step of inhaling a therapeutically effective amount of a gas mixture containing oxygen ($O_2$) and a portion by volume of 20 to 70% of xenon (Xe) to thereby treat the hypersensitivity in the humans or animals, wherein the hypersensitivity to pain is post-operative or post-traumatic hypersensitivity, wherein the hypersensitivity to pain is expressed as hyperalgesia or allodynia, and wherein the hypersensitivity to pain was induced by an opioid use by the humans or animals.

2. The method of claim 1, wherein the proportion of xenon is between 22 and 60% by volume.

3. The method of claim 2, wherein the proportion of xenon is between 25 and 60% by volume.

4. The method of claim 1, wherein the gas mixture consists only of a) oxygen and xenon or b) air and xenon.

5. The method of claim 1, wherein the gas mixture also contains nitrogen, helium, Nitric Oxide, krypton, argon or neon.

6. The method of claim 1, wherein the gas mixture contains a proportion by volume of oxygen of between 15 and 25%.

7. The method of claim 1 wherein the gas mixture is supplied for inhalation from a pressurized container at a pressure greater than 2 bar.

\* \* \* \* \*